US009255128B2

(12) United States Patent
Wedlich-Soldner et al.

(10) Patent No.: US 9,255,128 B2
(45) Date of Patent: Feb. 9, 2016

(54) NUCLEIC ACID FOR DETERMINING ACTIN STRUCTURES IN LIVING CELLS

(71) Applicant: Max-Planck-Gesellschaft zur Forderung der Wissenschaften E.V., Munich (DE)

(72) Inventors: Roland Wedlich-Soldner, Munich (DE); Michael Sixt, Munich (AT); Julia Riedl, Munich (DE); Alvaro Crevenna, Munich (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 14/593,274

(22) Filed: Jan. 9, 2015

(65) Prior Publication Data

US 2015/0113671 A1    Apr. 23, 2015

Related U.S. Application Data

(62) Division of application No. 12/744,822, filed as application No. PCT/EP2008/010093 on Nov. 27, 2008, now Pat. No. 8,957,029.

(30) Foreign Application Priority Data

Nov. 28, 2007  (EP) .................................... 07023084
Apr. 9, 2008  (EP) .................................... 08007067

(51) Int. Cl.
| | |
|---|---|
| *C07K 16/44* | (2006.01) |
| *C12N 15/09* | (2006.01) |
| *C40B 40/08* | (2006.01) |
| *C07K 14/395* | (2006.01) |
| *G01N 33/50* | (2006.01) |
| *G01N 33/569* | (2006.01) |
| *C07K 14/435* | (2006.01) |

(52) U.S. Cl.
CPC ......... *C07K 14/395* (2013.01); *C07K 14/43595* (2013.01); *G01N 33/502* (2013.01); *G01N 33/5026* (2013.01); *G01N 33/56966* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 6,583,275 B1 | 6/2003 | Doucette-Stamm et al. | |
| 2006/0046253 A1* | 3/2006 | Nakao ................... | C07K 14/39 435/6.18 |

OTHER PUBLICATIONS

Database Geneseq [Online], Jan. 1, 2004 "*E. faecium* protein sequence SEQ ID 4243," retrieved from EBI accession No. GSP:ADC94616 Database accession No. ADC94616 & U.S. Pat. No. 6,583,275 B1.
Database UniProt [Online], Jan. 1, 1998 "Unconventional myosin," XP002474757 retrieved from EBI accession No. UNIPROT:O24518 Database accession No. O24518.
Hostos et al., 1993, "Coactosin, a 17 kDa F-actin binding protein from *Dictyostelium discoideum*," Cell Motility and the Cytoskeleton, 26:181-191.
Haase et al., 2006, "Minigenes encoding N-terminal domains of human cardiac myosin light chain-1 improve heart function of transgenic rats," The FASEB Journal, 20:865-873.
Fehrenbacher et al., 2004, "Live Cell Imaging of Mitochondrial Movement along Actin Cables in Budding Yeast," Current Biology, 14:1996-2004.
Asakura et al., 1998, "Isolation and characterization of a novel actin filament-binding protein from *Saccharomyces cerevisiae*," Oncogene, 16:121-130.
Yang et al., 2002, "Actin cable dynamics in budding yeast," PNAS, 99(2):751-756.
Bresnick et al., 1991, "Evidence That a 27-Residue Sequence is the Actin-binding Site of ABP-120," The Journal of Biological Chemistry, 266(20):12989-12993.
Vandekerckhove et al., 1992, "Structural relationships of actin-binding proteins," Current Opinion in Cell Biology, 4:36-42.

* cited by examiner

*Primary Examiner* — Satyanarayana R Gudibande
(74) *Attorney, Agent, or Firm* — Riverside Law LLP

(57) ABSTRACT

The present invention relates to nucleic acids encoding peptides capable of binding to actin. The nucleic acids encoding the peptides are useful in methods for detecting actin in vitro or in living cells.

22 Claims, 5 Drawing Sheets

SEQUENCE LISTING

```
<160> NUMBER OF SEQ ID NOS: 15

<210> SEQ ID NO 1
<211> LENGTH: 10
<212> TYPE: PRT
<213> ORGANISM: Saccharomyces cerevisiae

<400> SEQUENCE: 1

Gly Val Ala Asp Leu Ile Lys Lys Phe Glu
1               5                   10

<210> SEQ ID NO 2
<211> LENGTH: 11
<212> TYPE: PRT
<213> ORGANISM: Saccharomyces cerevisiae

<400> SEQUENCE: 2

Met Gly Val Ala Asp Leu Ile Lys Lys Phe Glu
1               5                   10

<210> SEQ ID NO 3
<211> LENGTH: 16
```

<212> TYPE: PRT
<213> ORGANISM: Saccharomyces cerevisiae

<400> SEQUENCE: 3

Gly Val Ala Asp Leu Ile Lys Lys Phe Glu Ser Ile Ser Lys Glu Glu
1               5                   10                  15

<210> SEQ ID NO 4
<211> LENGTH: 17
<212> TYPE: PRT
<213> ORGANISM: Saccharomyces cerevisiae

<400> SEQUENCE: 4

Met Gly Val Ala Asp Leu Ile Lys Lys Phe Glu Ser Ile Ser Lys Glu
1               5                   10                  15

Glu

<210> SEQ ID NO 5
<211> LENGTH: 17
<212> TYPE: PRT
<213> ORGANISM: Saccharomyces mikatae

<400> SEQUENCE: 5

Met Gly Val Ala Asp Leu Ile Lys Lys Phe Glu Ser Ile Ser Lys Glu
1               5                   10                  15

Glu

<210> SEQ ID NO 6
<211> LENGTH: 17
<212> TYPE: PRT
<213> ORGANISM: Saccharomyces kudriavzevii

<400> SEQUENCE: 6

Met Gly Val Ala Asp Leu Ile Lys Lys Phe Glu Lys Ile Ser Asn Lys
1               5                   10                  15

Lys

<210> SEQ ID NO 7
<211> LENGTH: 17
<212> TYPE: PRT
<213> ORGANISM: Saccharomyces bayanus

<400> SEQUENCE: 7

Met Gly Val Ala Asp Leu Ile Lys Lys Phe Glu Lys Phe Ser Lys Lys
1               5                   10                  15

Glu

<210> SEQ ID NO 8
<211> LENGTH: 17
<212> TYPE: PRT
<213> ORGANISM: Saccharomyces castellii

<400> SEQUENCE: 8

Met Gly Val Ala Asp Leu Ile Gln Lys Phe Glu Lys Tyr Ala His Val
1               5                   10                  15

Asp

<210> SEQ ID NO 9
<211> LENGTH: 17
<212> TYPE: PRT
<213> ORGANISM: Candida glabrata -continued

```
<400> SEQUENCE: 9

Met Gly Val Ala Asp Leu Ile Lys Lys Phe Glu Gln Ile Ser Gln Glu
1               5                   10                  15

Ser

<210> SEQ ID NO 10
<211> LENGTH: 17
<212> TYPE: PRT
<213> ORGANISM: Vanderwaltozyma polyspora

<400> SEQUENCE: 10

Met Ser Val Ala Asp Leu Ile Lys Lys Phe Glu Asp Ile Ser Lys Ser
1               5                   10                  15

Gly

<210> SEQ ID NO 11
<211> LENGTH: 17
<212> TYPE: PRT
<213> ORGANISM: Saccharomyces kluyveri

<400> SEQUENCE: 11

Met Gly Val Ala Asp Leu Ile Lys Lys Phe Glu Thr Ile Ala Lys Lys
1               5                   10                  15

Glu

<210> SEQ ID NO 12
<211> LENGTH: 17
<212> TYPE: PRT
<213> ORGANISM: Kluyveromyces waltii

<400> SEQUENCE: 12

Met Gly Val Ala Asp Leu Ile Lys Lys Phe Glu Thr Ile Ala Lys Val
1               5                   10                  15

Asp

<210> SEQ ID NO 13
<211> LENGTH: 17
<212> TYPE: PRT
<213> ORGANISM: Kluyveromyces lactis

<400> SEQUENCE: 13

Met Gly Val Ala Asp Leu Ile Lys Lys Phe Glu Ser Ile Ala Lys Asp
1               5                   10                  15

Pro

<210> SEQ ID NO 14
<211> LENGTH: 17
<212> TYPE: PRT
<213> ORGANISM: Kluyveromyces marxianus

<400> SEQUENCE: 14

Met Gly Val Ala Asp Leu Ile Lys Lys Phe Glu Ser Ile Ala Lys Asp
1               5                   10                  15

Pro

<210> SEQ ID NO 15
<211> LENGTH: 17
<212> TYPE: PRT
<213> ORGANISM: Ashbya gossypii

<400> SEQUENCE: 15
```

```
Met Gly Val Ala Asp Leu Ile Arg Lys Phe Glu Ser Ile Thr Lys Glu
1               5                   10                  15
Asp
```

NUCLEIC ACID FOR DETERMINING ACTIN STRUCTURES IN LIVING CELLS

CROSS-REFERENCE TO RELATED APPLICATIONS

Figure 1:
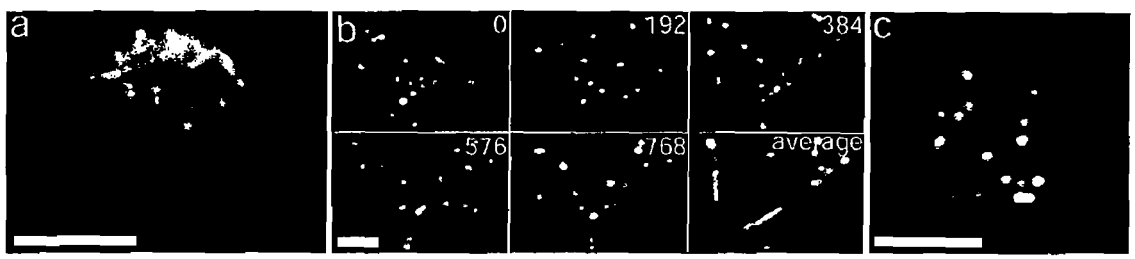
Figure 1:
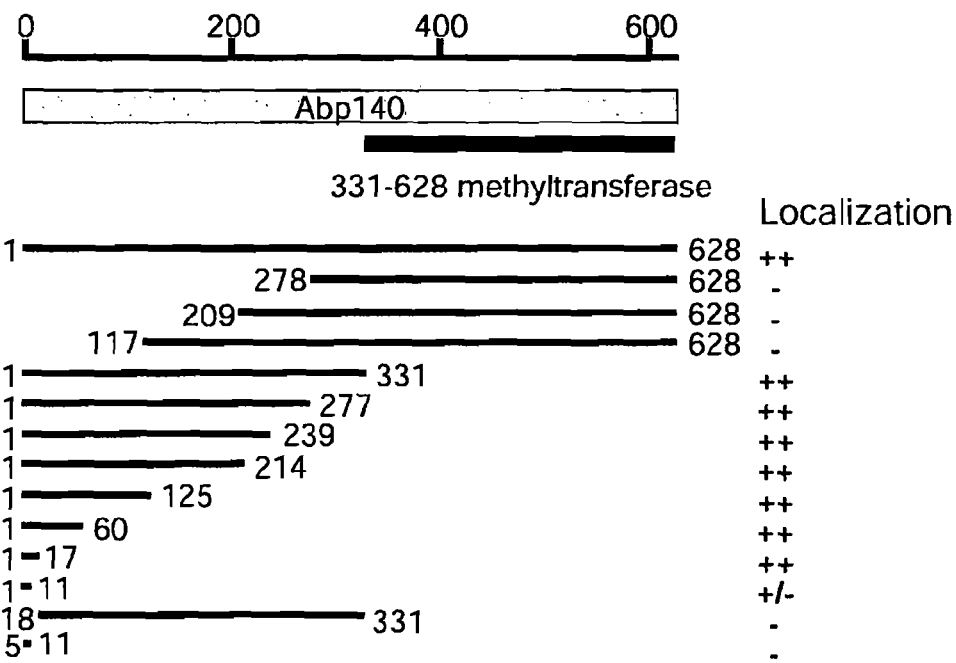

The present application is a divisional application of, and claims priority to, U.S. application Ser. No. 12/744,822, filed Jan. 10, 2011, issued as U.S. Pat. No. 8,957,029, which is a 35 U.S.C. §371 national phase application from, and claiming priority to, International Application PCT/EP2008/010093, filed Nov. 27, 2008, and published under PCT Article 21(2) in English, which claims priority to European Application Nos. 07023084.2, filed Nov. 28, 2007, and Ser. No. 08/007,067.5, filed Apr. 9, 2008, which applications are incorporated by reference herein in their entireties.

The present invention relates to novel peptides capable of binding to actin. The peptides are useful in methods for detecting actin in vitro or in living cells.

Actin is involved in many cellular processes such as morphogenesis, intracellular transport, cell division, muscle contraction and cell migration. The actin cytoskeleton is also altered in disease processes such as in invading tumour cells, myopathies or polycystic kidney disease[1-3]. In studying the various mentioned processes and conditions a reliable staining of the actin cytoskeleton is essential. In most cases staining of fixed cells with the F-actin binding compound phalloidin coupled to fluorescent dyes is used. However, some cells such as the plant pathogenic fungus *Ustilago maydis*, cannot be stained by phalloidin[4]. In addition it is often desirable to image actin in living cells. The dynamics of actin filaments are much more sensitive readouts for cytoskeletal organization and processes such as cell polarization or cell migration can only be properly studied through analysis of cytoskeletal dynamics.

To study actin dynamics, researchers have relied either on the injection of fluorescently labelled actin or small amounts of phalloidin[5,6] or on the use of GFP fusion proteins. In the former case application is limited to large cells that can be injected, requires specialized equipment, relatively expensive probes and quantitative analysis is complicated by difficult control of the fluorescent actin concentration. Speckle analysis has provided a powerful tool for the detailed study of actin polymerization dynamics with only trace amounts of labelled molecules. Various GFP fusion proteins have been used to visualize actin in living cells. Most often actin itself has been fused to GFP but all documented actin-GFP fusion proteins exhibit reduced functionality and they can only be used in combination with non-tagged actin present[7]. Even in cases where cells are not visibly affected by actin-GFP expression it is not certain whether actin dynamics is partially affected. Therefore, while actin-GFP can be used in several cell types to monitor actin distribution it is to be used with great care if studying actin dynamics. Actin-GFP is also limited in its application as it exhibits a strong background staining from labelled actin monomers and therefore requires low expression levels. Alternatively fusion of GFP to several actin binding domains have been used, notably from moesin in *Drosophila*[8], LimE in *Dictyostelium*[9], Abp120 in *Dictyostelium* and mammalian cells[10,11] and utrophin in *Xenopus*[12]. In plants fusions to the actin binding domains of mouse talin[13] or fimbrin[14] have been used but each seems to stain only a subset of actin structures and can lead to artificial bundling of actin if expressed at high levels[15,16]. In general the used fusion proteins are still quite large and are restricted to cells that can be transfected or injected.

The present invention describes the identification and application of short novel peptides, which specifically stain F-actin structures in a wide range of cell types when coupled to labelling groups such as fluorescent proteins or chemical labelling groups. Preferably, these novel peptides bind efficiently to actin and do not interfere with actin dynamics in vitro and in vivo. The novel peptides were validated by visualizing and quantifying actin dynamics in several sensitive biological processes such as neuronal growth cone formation or dendritic cell migration. The novel peptides of the present invention may be easily obtained by chemical synthesis or recombinant methods and allow visualization of actin dynamics in non-transfectable cells, such as primary neutrophils.

The novel peptide probes are ideally suited as a marker for F-actin in living as well as fixed cells. Preferably, the probe is a 17 amino acid (aa) fragment of the yeast actin binding protein Abp140 that faithfully stains F-actin without interfering with actin polymer dynamics.

A first aspect of the present invention refers to a peptide having the amino acid sequence (I)

$$(M)_n GVADLIKKFE$$

wherein n is 0 or 1, or a variant thereof.

A further aspect of the present invention refers to a peptide having the amino acid sequence (II)

$$(M)_n GVADLIKKFESISKEE$$

wherein n is 0 or 1, or a variant thereof.

Amino acid sequences (1) and (11) are derived from the N-terminal portion of the actin binding protein Abp140 from the yeast *S. cerevisiae*. In addition to these sequences, the present invention refers also to variants thereof, e.g. to variants derived from other fungal species, e.g. as disclosed FIG. 1e of the present application. In preferred variants of the peptides (I) and (II), amino acid residues 2-10 are selected such that an α-helical structure is formed. Further, the invention encompasses peptides with one, two, three or even more amino acid substitutions within amino acid residues 2-11 of peptides (1) and (II) and optionally one, two, three, four or even more amino acid substitutions within amino acid residues 12-17 of peptide (II). For example, in peptide (I) the amino acid residue G at position 2 may be replaced by S and/or the amino acid residue K at position 8 may be replaced by Q or R. In peptide (II) additional amino acid substitutions may occur e.g. at positions 12 to 17, e.g. a substitution of S at position 12 by K, Q, D and/or T, a substitution of I at position 13 by F or Y, a substitution of S at position 14 by A or T, a substitution of K at position 15 by N, H, or Q, a substitution of E at position 16 by K, V, S or D, and/or a substitution of E at position 17 by K, D, S, G and/or P.

The peptides of the present invention are preferably capable of efficiently binding to actin, particularly to F-actin. The dissociation constant $K_d$ is usually ≤50 μM, preferably ≤10 μM and more preferably ≤5 μM.

The peptides of the invention may be linear or cyclic peptides. Optionally the peptides may comprise modified or non-genetically encoded amino acid residues. The peptides preferably have a length of up to 120, preferably up to 50, and more preferably up to 20 amino acid residues. More preferably, the peptides are selected from the N-terminal portion of fungal Abp140 polypeptides, e.g. from *S. cerevisiae*, or actin-binding fragments thereof.

The peptides of the invention may be monomeric or multimeric. Multimerisation of the peptides may comprise the use of linkers. The linkers may be naturally occurring or synthetically produced peptide sequences having a length of e.g. 1 to 15, preferably 1 to 10 amino acids. Alternatively, the linkers may be non-peptidic moieties, e.g. synthetic amino acids, chemical linkers, oligo- or poly(alkylene)oxide moieties.

The peptides are preferably coupled to heterologous molecules, e.g. labelling groups, which allow detection of the peptides. In one embodiment, the heterologous molecule is a peptide or polypeptide, e.g. a labelling peptide such as the FLAG epitope or a labelling polypeptide such as GFP or any variant thereof. In another embodiment, the heterologous molecule may be a non-peptidic molecule, e.g. a chemical labelling group, particularly a fluorescent chemical labelling group such as fluoresceine, rhodamine or another fluorescent labelling group. The heterologous molecule may be coupled to the N- and/or to the C-terminus of the peptides (I) or (II). For example, fluorescent polypeptides such as GFP or mRF-Pruby may be genetically fused to the C-terminus of the peptide without affecting actin binding. Further, fluoresceine isothiocyanate (FITC) may be coupled to the N-terminus of the peptides also without affecting binding to actin. Furthermore, peptidic linker sequences such as the sequence C-G may be added to the C-terminus for functional coupling of heterologous molecules via the SH-group of cysteine.

The peptides of the invention may be synthesized by chemical methods, e.g. using a solid phase peptide synthesizer or—particularly in the case of peptides fused to heterologous peptides or polypeptides—by recombinant methods in suitable host cells.

Thus, a further aspect of the present invention refers to a nucleic acid molecule encoding a peptide as described above, particularly a peptide fused to a heterologous peptide or polypeptide, particularly to a fluorescent polypeptide. For example, the nucleic acid molecule may be a single- or double-stranded DNA or RNA molecule. Preferably, the nucleic acid molecule is operatively linked to an expression control sequence, i.e. a sequence which is sufficient for effecting expression in a suitable host cell, e.g. a prokaryotic or eukaryotic host cell. Preferably, the expression control sequence is capable of providing expression in a vertebrate host cell, particularly in a mammalian host cell.

Still a further aspect of the present invention refers to recombinant cells transfected or transformed with a nucleic acid molecule as described above. The recombinant cell may be a prokaryotic cell, e.g. an *E. coli* cell, or a eukaryotic cell, e.g. a fungal cell, an animal cell, particularly a vertebrate cell such as an insect, fish, bird or mammalian cell or a plant cell. Transfection or transformation of the recombinant cell may be carried out by standard methods known in the art, e.g. calcium phosphate precipitation or electroporation.

Still a further aspect of the present invention is a non-human transgenic organism transfected or transformed with the nucleic acid molecule as described above. The transgenic organism may be a fungus, an animal, e.g. a nematode like *C. elegans*, an insect such as *Drosophila*, a fish such as *Danio rero*, or a mammal such as a rodent, e.g. a mouse or a rat. On the other hand, the organism may be a plant such a *Arabidopsis thaliana*.

The peptide, nucleic acid molecule, recombinant cell or non-human transgenic organism as described above are useful for the detection of actin, preferably for the detection of actin within a cell, particularly within a living cell. By means of the present invention, actin-associated processes such as cell migration, cell division and/or cell differentiation may be detected. Other relevant applications are research on cell polarity, neuronal development, muscle development, cell-matrix interaction, cancerogenesis, immune reactions, e.g. of neutrophils, T-cells or dendritic cells etc.

Further, the present invention has also applications in pharmaceutical research. As the actin cytoskeleton is a key component for nearly all types of cellular morphogenesis, actin may be used as marker or target in cell-based screening methods and therapeutic approaches. Thus, the present invention is suitable for application in cell-based screens for drugs, e.g. cancer drugs, or in the study of actin-based diseases such as Myopathies or polycystic kidney disease.

Furthermore, the peptides of the present invention may be used for the modulation of actin-associated processes in therapeutic applications. In this embodiment, the peptides may serve as targeting molecules for the actin cytoskeleton. The peptides may be coupled to effector groups such as oxygen radical producers or caged compounds which can be activated in a regulated way. Further, cellular signalling molecules or cellular regulators or cytoskeleton modulators may be used as effector groups, to redirect cellular functions and/or cellular structure. For example, actin nucleators, organelle membrane proteins, GTPase regulators such as activators of Rho-type GTPases may be linked to the peptides of the invention and targeted to actin, thereby increasing the effects on actin-dependent processes.

Further, multimeric peptides, e.g. dimeric or trimeric peptides, may be used to modulate cellular actin structures and thus cellular processes.

Furthermore, the above-described peptides may be used in drug screening, particularly when coupled to a labeling group. Particularly preferred is the use in high throughput drug screening assays as a readout system to detect phenotypic responses of a cell to a screening compound, e.g. alterations in the cellular actin structure.

Further, the present invention shall be explained in more detail by the following Figures and Examples.

FIGURE LEGEND

FIG. 1 Identification of Lifeact. a) TIRF image of Abp140-GFP distribution in an unpolarized yeast cell. Scale bar: 5 µm. b) Fast blinking of Abp140-GFP signals on actin structures. Time in ms, scale bar: 2 µm. c) distribution of the minimal Lifeact-G in a yeast cell. Scale bar: 5 µm. d) Schematic organization of Abp140 and illustration of tested localization constructs. Numbers indicate amino acid positions. Localization scores: ++ comparable to full-length protein, – not localized, +/– localizes mostly to actin patches. e) ClustalW alignment of Lifeact with homologous sequences from related fungi.

Figure 2:
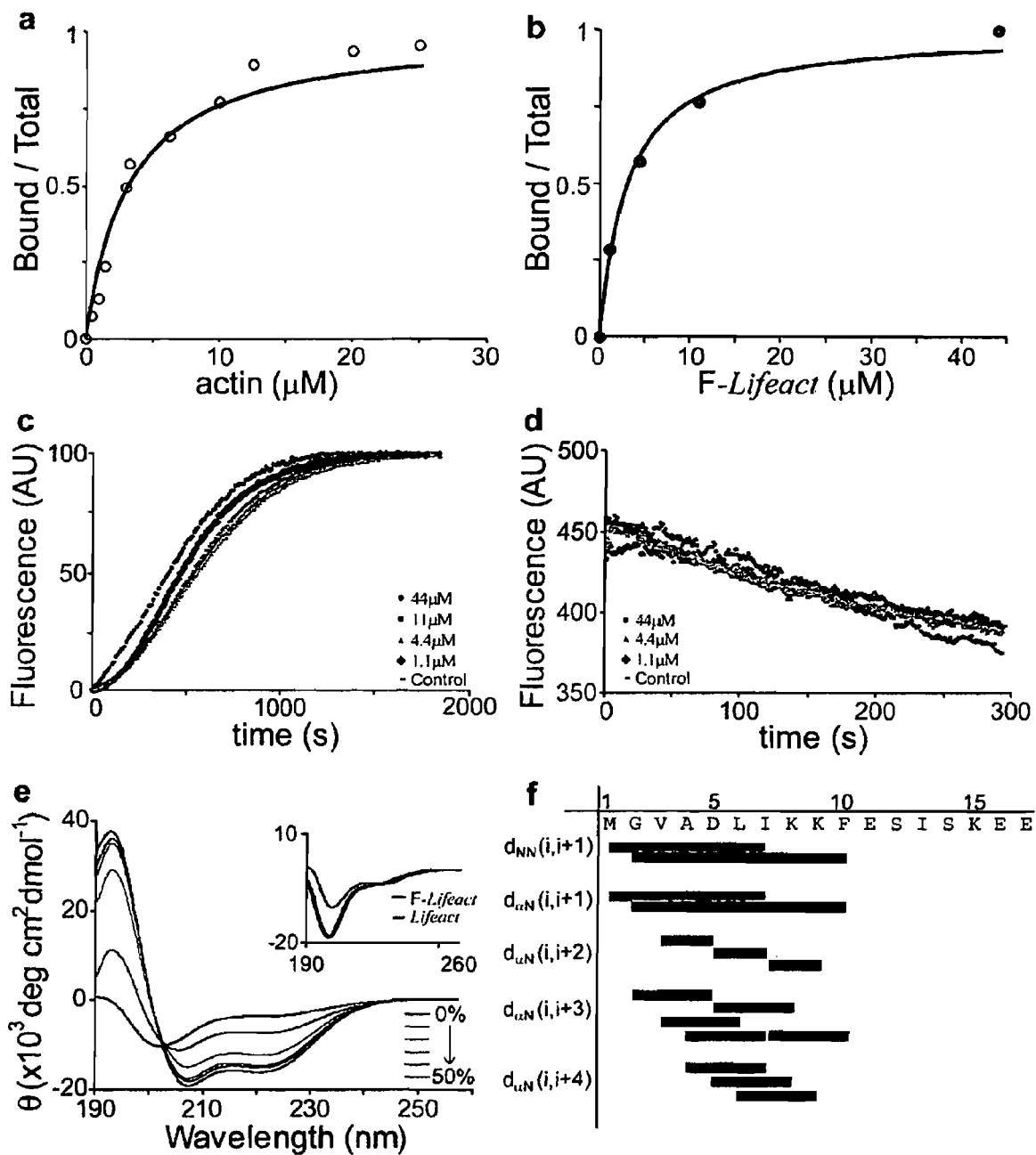

FIG. 2 Biochemistry of Lifeact. a) Measurement of F-Lifeact binding to rabbit muscle F-actin. Shown is the relative fluorescence of peptide co-sedimented with various concentrations of F-actin. b) Measurement of F-Lifeact binding to G-actin. Binding was determined by measuring relative changes in pyrene-G-actin fluorescence in the presence of varying amounts of F-Lifeact. c) Actin polymerization assay. Polymerization of pyrene-actin was followed in the presence of indicated concentrations of F-Lifeact. d) Actin depolymerization assay. Depolymerization of pyrene-F-actin was followed after dilution below the critical concentration in the presence of indicated concentrations of F-Lifeact. e) Circular Dichroism (CD) measurements on F-Lifeact upon titration with 0-50% TFE. Inset: CD on F-Lifeact and Lifeact without TFE. f) Short and medium range NOE connectivities involving the NH and C.°H protons (21,29). Blue bars represent measurements on F-Lifeact at pH 7.1, red bars represent measurements on Lifeact at pH 3.0 in the presence of 15% (v/v) HFP-$d_2$.

Figure 3:
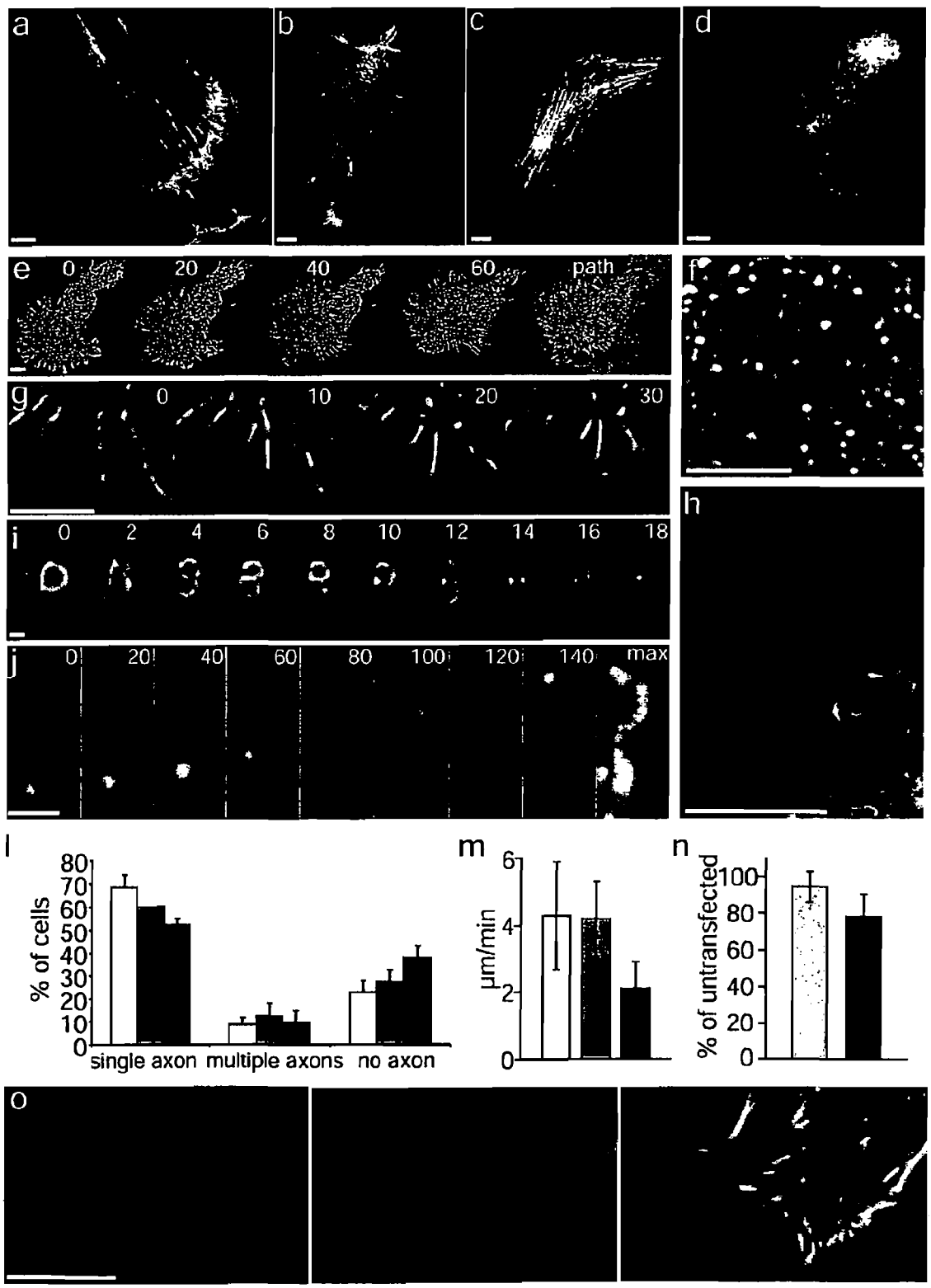

FIG. 3 Lifeact-GFP: visualization and functional characterization in vivo. a-j) Lifeact G was transiently expressed in mouse embryonic fibroblasts (a, j), primary rat hippocampal neurons (b, f, g, h), MDCK cells (c, i) and mouse dendritic cells (d, e) and imaged with TIRF microscopy. e) Time sequence of a dendritic cell chemotaxing towards a chemokine source. f) Cortical actin network of a hippocampal neuron. g) Time series of filopodial dynamics in a hippocampal neuron. h) Dynamic snapshot of a filopodium: green shows signals that decrease in intensity between two frames (3 s apart), red shows signal that increases in the same time span. j) Time series of an MDCK cell undergoing cytokinesis, showing Lifeact-G staining in the contractile ring. j) Time series of actin patch movement within the cortex of a fibroblast. l-n) Functional influence of transiently expressed Lifeact-GFP. Open bars: untransfected; grey bars: Lifeact-G; black bars: actin-GFP. Bars show values +/−SE (l) or +/−SD (m, n). (l) Neuronal polarization 3 days after transfection. m) Velocity of lamellipodial retrograde actin flow in fibroblasts. n) Chemotactic speed of dendritic cells. Numbers are given in percent relative to untransfected cells. o) Widefield microscopy of MDCK cells double transfected with actin RFP and Lifeact-G. Scale bars: 5 µm except 3j: 1 µm.

Figure 4:
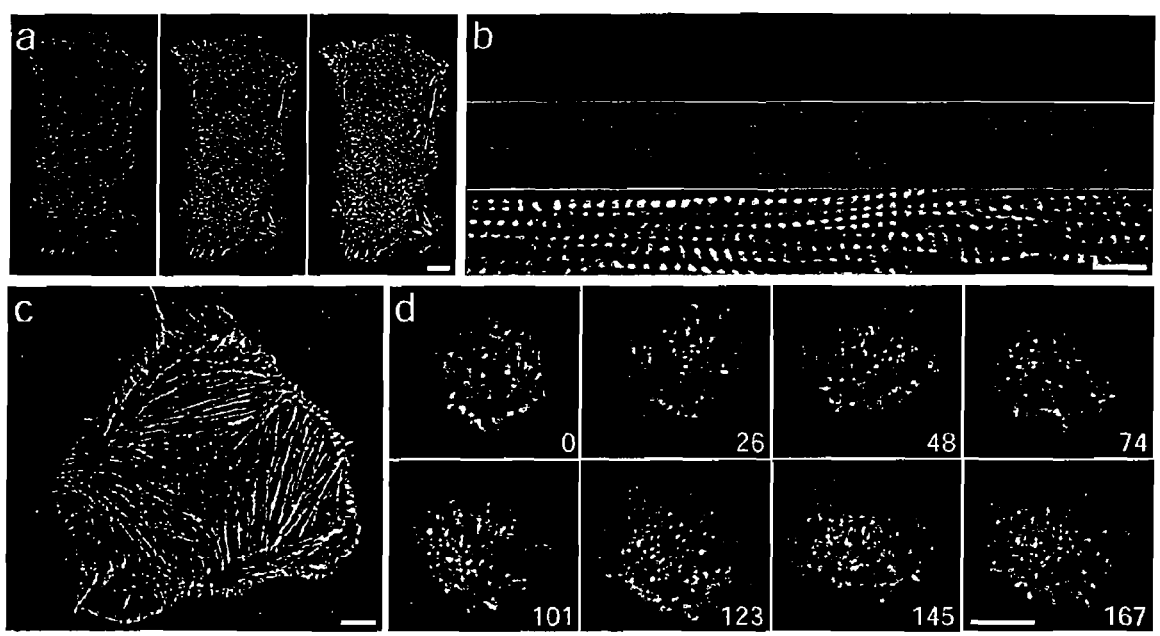

FIG. 4 F-Lifeact staining in fixed and living samples. MDCK cells (a) and cryo sections of mouse skeletal muscle (b) were fixed with PFA and double stained with F-Lifeact and phalloidin-Cy3. Mouse embryonic fibroblasts (c) and human primary neutrophil granulocytes (d) were scrape loaded with F-Lifeact, re-plated and subsequently visualized with TIRF microscopy. Scale bars: 5 µm.

Figure 5:
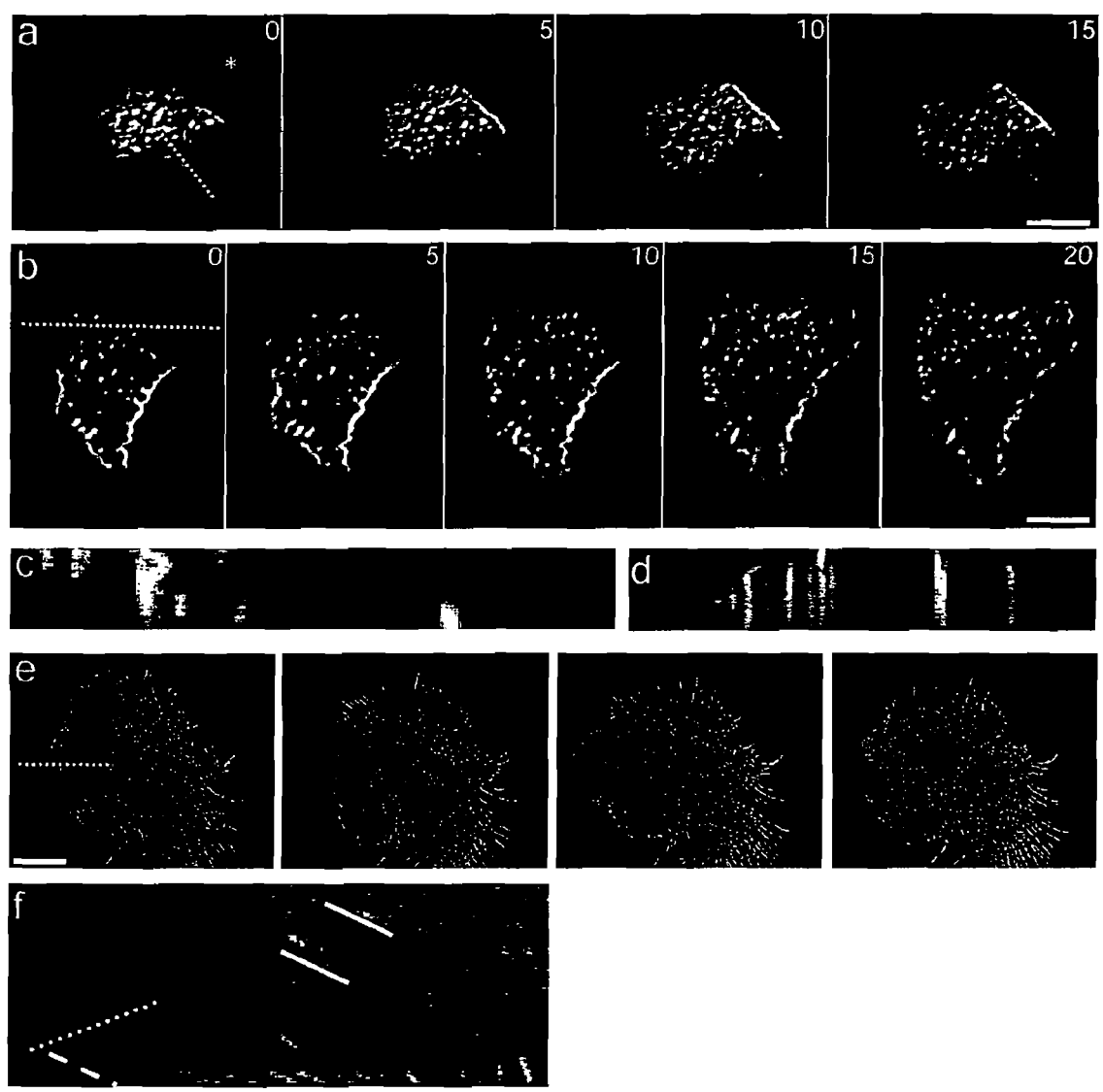

FIG. 5 Actin dynamics in leukocytes
a, b) Time series of primary human neutrophils scrape loaded with F-Lifeact spreading on plated immune complexes. c, d) kymographs of the indicated regions in (a) and (b), respectively. e) Lifeact-G expressing mouse dendritic cell undergoing lamellipodial extension and retraction. f) Kymograph of the indicated region in e). Solid lines: retrograde actin flow, dotted line: lamellipodial extension and dashed line: lamellipodial retraction. Size bars: 5 µm.

EXAMPLES

1. Material and Methods

Yeast Strains and Plasmid Constructions.
All Abp140-GFP plasmids were expressed in the S288C yeast background and based on the pRS315 backbone (LEU2, CEN). Expression was driven by the native Abp140 promoter (300 bp) and a short GS linker was generated between Lifeact and GFP. For expression in mammalian cells the Lifeact sequence was cloned into pEGFP-N1 (Clonetech) or the respective plasmid with mRFPruby replacing GFP. In both cases the linker GDPPVAT was generated between Lifeact and the fluorescent protein. Actin-GFP was used in the same plasmid backbones. Cells were grown at 24° C. and observed from logarithmically growing cultures (OD<0.8). Standard yeast media and procedures were used.

Microscopy and Image Acquisition.
TIRE images were captured on an iMic-stand from Till photonics with an 1.45 NA 100× objective from Olympus. A 300 mW Argon laser and a 20 mW DPSS 561 nm laser were selected through an AOTF. A 2-axis scan head (Yanus II) was used to digitally adjust the TIRE angle. Images were collected with a cooled Imago QE CCD camera. Acquisition was controlled by the TILLvisION software package. Confocal images were collected on a standard Leica SP2 setup. Epifluorescence images were collected on a Zeiss axiovert 200M stand equipped with a climate control chamber from EMBL.

Image Processing and Data Analysis.
All image processing steps were performed in Metamorph (Molecular Devices). For visualization purposes sequences were routinely processed by sequential application of a local background subtraction filter and a 3×3 gauss low pass filter. Color overlays and kymographs were created with the respective functions in Metamorph.

Proteins.
Muscle actin, non-muscle actin, α-actinin and pyrene actin were purchased from Cytoskeleton, Inc. Actin was diluted to working concentrations in G buffer (2 mM Tris HCl, pH 8.0, 0.2 mM ATP, 0.1 mM $CaCl_2$, 0.5 mM DTT).

Actin Binding.
Polymerization of actin was induced by addition of 0.1 volume 10×KMEI buffer (50 mM KCl, 1 mM $MgCl_2$, 1 mM EGTA, 10 mM imidazole HCl, pH 7.0) and incubation for >1 h at room temperature (RT). 44 µM of F-Lifeact was incubated 30 min with F-actin and then spun 30 min at 350,000×g at room temperature. The supernatant was removed and the pellet resuspended in 100 µl of 1×KMEI buffer. The amount of peptide was measured in a Cary Eclipse Fluorescence Spectrophotometer with excitation/emission set for FITC at 495 nm/520 nm. The bound/total ratio was calculated as the signal from the pellet divided by the total signal. The $K_d$ was obtained by fitting to a hyperbolic curve.

Binding to G-actin was determined from a spectral scan of pyrene actin in the presence of varying amounts of F-Lifeact. Averages of 5 emission scans between 370 nm and 500 nm were used with excitation set to 365 nm. The bound/total ratio was calculated from the absolute emission difference at 385 nm between a given Lifeact concentration and the control divided by the maximum difference observed. The $K_d$ was obtained by fitting to a hyperbolic curve.

Actin Polymerization and Depolymerization.
For polymerization assays, 20% pyrene-labelled actin was centrifuged at 350,000×g for 30 min at 24 C to remove any nucleation seeds. Ca to Mg exchange was done adding 0.1V of 10× ME buffer (50 µM $MgCl_2$, 0.2 mM EGTA) for 2 min. Polymerization was promoted by addition of 0.1V 10×KMEI buffer. The final volume was 100 µl. Pyrene fluorescence was monitored spectroscopically (excitation 365 nm, emission 407 nm). To test the effect of F-Lifeact on polymerization different amount of F-Lifeact were added to the pyrene-actin after centrifugation and incubated for 5 min. Depolymerization was measured by monitoring pyrene fluorescence after diluting 100% pyrene-labelled F-actin in 1×KMEI buffer to <0.2 µM. To test its effect on depolymerization the indicated concentrations of F-Lifeact were pre-incubated with F-actin for 5 min before dilution.

Far UV CD Spectroscopy.
CD measurements were performed on a Jasco J-715 spectropolarimeter with a peptide concentration of 4.4 µM.

NMR Sample Preparation and Spectroscopy.
For NMR F-Lifeact was dissolved in PBS pH 7.1. Unlabelled Lifeact was dissolved in PBS at pH 3. In order to stabilize secondary structure of the peptide, 15% (v/v) of 1,1,1,3,3,3-hexafluoro-2-propanol-$d_2$ (HFP-$d_2$) was added to the sample of the unlabeled peptide. 10% of $D_2O$ (v/v) was added to all samples. NMR measurements were carried out at 600 MHz on a Bruker DRX-600 spectrometer equipped with a cryoprobe at 300K. 2D nuclear Overhauser effect (NOESY) spectra were carried out with mixing time of 100 ms, and total correlated spectroscopy (TOCSY) spectra were recorded with DIPSI2 mixing sequence of 35 ms and 80 ms duration (for the unlabelled peptide in alcohol/water and labelled peptide in PBS). Water suppression was carried out using the WATERGATE sequence. Sequence specific resonance assignments were carried out as in[21]. Amino acids spin systems were identified by analysis of TOCSY spectra. NOESY spectra were used to observe contacts <5 Å.

Cell Culture.

Mouse primary dendritic cells were generated from flushed bone marrow suspension as described previously[30]. At day 8-10 cells were nucleofected using the primary mouse T cell kit and the Amaxa nucleoporator according to the manufacturers recommendations and immediately after transfection 200 ng/ml LPS were added over night and cells were subsequently sorted into GFP positive and negative fractions by using fluorescent activated cell sorting. MDCK cells and mouse embryonic Fibroblasts were grown according to standard procedures and transfected using lipofectamine.

Chemotaxis Assays.

PureCol™ gels containing mature dendritic cells were cast as described previously. Gels were overlayed with 50 µl of 0.6 µg/ml CCL19 (R&D Systems) in RPMI, 10% FCS and imaged on an inverted Axiovert 40 (Zeiss) microscopes, equipped with custom built climate chambers (5% CO2, 37° C., humidified). Under agarose dendritic cell migration was performed as described[31]. Briefly, dendritic cells were added into wells punched into an agarose layer. Recombinant CCL19 was added into the adjacent well and, following the chemokine gradient, the cells entered the space between agarose and coverslip. Chemotaxing cells were subsequently imaged with TIRF microscopy.

Culturing, Transfection and Classification of Primary Hippocampal Neurons.

Primary hippocampal neurons were isolated from rat embryos as previously described. Briefly, hippocampi derived from E18 rats were dissected, trypsinized, and dissociated. Directly after dissociation, $5 \times 10^5$ hippocampal neurons were transfected by the Amaxa nucleofector system using 3 µg of highly purified plasmid DNA of pEGFP-Lifeact, pEGFP-actin or pEGFP-N2. The neurons were then immediately plated onto poly-L-lysine-coated glass coverslips in 6 cm petri dishes containing minimal essential medium (MEM) and 10% heat-inactivated horse serum. The cells were kept in 5% $CO_2$ at 36.5° C. 6-12 hrs after plating the glass coverslips were then transferred into 6 cm petri dishes containing astrocytes in MEM and N2 supplements and kept in culture for 2DIV.

Neurons were categorized into three stages: neurons with a single axon, multiple axons or no axon. A neurite length >35 µm was used as threshold to define the axon. Developmental stages were observed by live cell microscopy as described.

Human Neutrophils and IC Induced Spreading

Human peripheral blood neutrophils were isolated by density centrifugation using a Pancoll™ gradient. Briefly, 10 ml blood containing EDTA was diluted in 10 ml PBS and layered on 10 ml pancoll. After 30 min centrifugation at 500 g neutrophil were separated from the erythrocyte rich pellet by dextran sedimentation. Residual erythrocytes were eliminated by hypertonic lysis and after washing in PBS, neutrophils were resuspended in RPMI containing 0.5% low endotoxin bovine serum albumin. Neutrophil purity was routinely ~95% as assessed by forward and side scatter with flow cytometry as well as by morphological analysis.

To form ICs in vitro, glass slides were coated with 5 mg/ml ovalbumin in PBS overnight at 4° C. followed by washing and incubation in rabbit anti-ovalbumin serum at 50 µg/ml specific IgG for 2 h at room temperature. F-Lifeact loaded neutrophils were subjected to ICs in the presence of 10 ng/ml tumour necrosis factor-α to study actin reorganization in response to ICs.

2. Results 2.1 Identification of a Novel F-Actin Binding Domain in Abp140

Among all actin binding proteins from the yeast S. cerevisiae only Abp140-GFP has been shown consistently to localize to both actin patches and actin cables (17,18). As Abp140 is expressed at low levels and actin cables are mostly oriented along the cell cortex, it is very difficult to visualize. Abp140-GFP labelled cables with conventional epifluorescence microscopy and we decided to use Total Internal Reflection (TIRF)-microscopy instead. With this technique we were able to improve image contrast greatly and to observe the full extent of cortical actin distribution for the first time (FIG. 1a). The improved signal to noise ratio also allowed us to image actin dynamics at high temporal resolution. Interestingly we found that at frame rates above 10/s Abp140-GFP exhibited a strong blinking behaviour (FIG. 1 b) indicating a relatively low affinity of Abp140-GFP to actin.

Abp140 has a highly conserved methyltransferase domain at its C-terminus and a charged N-terminal half that has no apparent similarity to proteins form higher eukaryotes. Using TIRF imaging as readout we set out to identify the actin binding domain of Abp140 through serial deletions. When we fused various domains of Abp140 to GFP we were surprised to find that a short N-terminal peptide of only 17aa was sufficient to achieve actin localization comparable to the full-length protein (FIG. 1c, d). An even shorter 11aa peptide still retained actin binding properties but was nearly exclusively restricted to actin patches. This might be due to reduced actin affinity of the peptide so that only structures of high actin density could be stained. Interestingly, in contrast to the rest of the N-terminal part of Abp140, the identified 17aa peptide is highly conserved in Abp140-homologues from closely related fungi (FIG. 1e), indicating that this short sequence constitutes a conserved actin binding motif. No other protein in yeast or any other organisms contains related sequences. The identified peptide is the shortest marker for actin in living cells identified so far. We termed it Lifeact and since it was so effective in staining F-actin structures in yeast cells we reasoned that Lifeact might be a good candidate for a general actin marker in eukaryotic cells. To this end we constructed mammalian expression vectors for Lifeact-GFP and Lifeact-mRFPruby and also chemically synthesized the 17aa peptide and tagged it with fluorescein (F-Lifeact) at its N-terminus.

2.2 Biochemical Properties of the Lifeact Peptide

An effective probe for actin should have no or very little influence on the dynamics of actin polymerization and depolymerization. We therefore tested the properties of F-Lifeact in in vitro assays for actin dynamics. To determine the affinity of Lifeact to filamentous actin we performed an F-actin co-sedimentation assay. The amounts of peptide in the pellet and in the supernatant were measured spectroscopically. F-Lifeact bound to muscle actin with a dissociation constant ($K_d$) of 3.1±0.7 µM (mean±95% CI, n=3, FIG. 2a). The $K_d$ for non-muscle actin was 5.4±2.6 µM. This low affinity is consistent with the blinking behaviour observed in yeast cells. We also determined whether F-Lifeact binds to G-actin by monitoring fluorescence quenching of pyrene-labelled actin as a function of peptide concentration. We found that F-Lifeact bound to G-actin with a similar affinity of 3.0±0.8 µM (FIG. 2b).

We tested possible effects of the peptide on actin polymerization in pyrene assays (19). Concentrations from 1.1 µM to 11 µM of Lifeact had no visible effect on nucleation and elongation of F-actin (FIG. 2c). Only at 44 µM a difference in nucleation could be observed where the lag phase of polymerization was reduced from 100 s to approximately 30 s (FIG. 2c, black circles). Even at 44 µM peptide the elongation rate was not affected. We also tested potential effects on actin depolymerization by diluting pyrene labelled F-actin below the critical concentration in the presence of peptide. The difference in depolymerization rates of F-actin incubated with either low (1.1 µM) or high (44 µM) concentrations of F-Lifeact was less than 10% (FIG. 2d).

To investigate whether Lifeact adopts a specific structure that allows it to bind to actin we examined its secondary structure by Far-UV Circular Dichroism (CD) spectroscopy and NMR. F-Lifeact dissolved in PBS had a slight propensity of adopting an α-helical structure (FIG. 2e blue line), which could be stabilized by increasing amounts of trifluorethanol (TFE) (FIG. 2e). Titration with TFE showed the typical α-helix polarization pattern (local minimum at 222 nm) at only 10% (FIG. 3e) indicating a strong tendency of F-Lifeact to form an α-helix. Unlabelled Lifeact peptide was not soluble in PBS and was therefore dissolved in 10% acetic acid (pH 3). In this buffer Lifeact did not show any helical properties (FIG. 2e inset). However, addition of 15% hexafluoro-2-propanol (HFP) stabilized the secondary structure of Lifeact and analysis of 2D NOESY NMR spectra of HFP stabilized peptide showed a typical α-helix signature from residues 2 to 10 (FIG. 2f red bars). In contrast, F-Lifeact at neutral pH formed a nascent helix covering residues 1-7 (FIG. 2f blue bars), where only short range NH—NH NOE contacts were observed (20). These features of Lifeact are reminiscent of the behaviour of thymosin $\beta_4$, a 42 amino acid G-actin binding peptide, which forms a nascent helix in water that can be further stabilized by the addition of an alcohol (21). Crystallographic analysis shows that one of nascent helices of thymosin $\beta_4$ becomes a fully stable α-helix after binding to G-actin (22,23).

2.3 Use of Lifeact-GFP in Mammalian Cells

To express Lifeact in mammalian cells we introduced the coding DNA for the 17aa peptide into the pEGFP-N1 backbone. The resulting plasmid expressing a Lifeact-GFP fusion (Lifeact-G) from the strong CMV promoter was then transiently transfected in a wide range of primary and immortalized mammalian cell types derived from different species. We covered all major cell lineages by transiently expressing Lifeact-G in immortalized mouse embryonic fibroblasts, Madin-Darby canine kidney (MDCK) cells (immortalized epithelial cells), primary rat hippocampal neurons and primary mouse dendritic cells (haematopoietic lineage of the myeloid type).

In all cells tested we obtained a clear and contrasted signal on F-actin structures that matched the patterns previously reported for these cell types (FIG. 3a-d). We noted no signs of cytotoxicity and transiently as well as stably transfected lines of MDCK and mouse embryonic fibroblasts maintained their normal morphology and did not show signs of growth retardation.

We next wanted to test if Lifeact-G is a universal marker of F actin or if it selectively associates with subsets of actin structures. TIRF microscopy was used to image cortical F-actin structures dynamically with high resolution. In fibroblasts and dendritic cells the flow of dynamic lamellipodial actin was prominent at the cell periphery (FIG. 3a, e), while stable stress fibres formed in the cell body of tightly adherent fibroblasts (FIG. 3a). Neurons were rich in dynamic filopodia (FIG. 3b) that frequently underwent kinking (FIG. 3g) and torsion (FIG. 3h). The surface of neuronal cell bodies was covered in an isotropic network of actin filaments (FIG. 3f) that was also seen in all other cell types. MDCK cells showed stress fibres and circumferential actin belts at the cell periphery (FIG. 3c). During cytokinesis Lifeact-G highlighted the contractile rings of MDCK cells observed by conventional wide field optics (FIG. 3i). In all four cell types we also saw numerous bright F-actin patches that associated with the cortical network of actin cables (FIG. 3f) and were highly dynamic. In most cases the behaviour of theses dots was reminiscent of actin patches in S. cerevisiae with patches appearing and disappearing without significant lateral motion, but occasionally we could observe dots that moved directionally over larger distances (FIG. 3j).

To test if Lifeact-G compromises cytoskeletal functions quantitatively, we measured three parameters that are sensitive readouts for actin dynamics: neuronal polarization, retrograde flow within the leading lamella of fibroblasts and directed migration of dendritic cells along gradients of chemokine. In all cases we compared Lifeact-G with actin GFP expressed from the same vector (CMV promoter). Neuronal polarization was slightly affected by the expression of Lifeact-G (FIG. 3l, 60.1±0.2% cells formed one axon compared to 69±9% of mock transfected cells), but much less than by a comparable expression of actin-GFP (52±4%). The speed of retrograde flow in lamellipodia of Lifeact-G transfected fibroblasts was indistinguishable from untransfected cells at 4 µm/min, whereas it was reduced to about half in actin-GFP expressing cells (FIG. 3m). Finally Lifeact-G had no effect on the speed of chemotactic dendritic cell migration in a 3-dimensional collagen matrix, while actin-GFP expressing cells migrated slightly slower and less directionally (FIG. 3n and not shown).

Next we directly compared the quality of Lifeact-G labelling to that of the actin GFP fusion. We performed double transfections with Lifeact-G and actin-mRFPruby (FIG. 3o) (24) or with Lifeact-mRFPruby and actin-GFP (not shown) in fibroblasts. Both probes showed overlapping patterns with slightly different characteristics: while in TIRF microscopy both labels gave a clear signal, the actin-GFP was slightly blurred in wide field optics due to high background signal from G-actin. In contrast, Lifeact-G signal showed high contrast indicating that G-actin is not significantly bound by the peptide in living cells. Consequently the retrograde flow of lamellipodial actin in fibroblasts was easily visible with Lifeact-G in a Widefield setup, whereas actin-GFP could not be used to track actin flow reliably (not shown).

2.4 Labelling of Cells with Fluorescent Peptides

The short Lifeact peptide can be readily chemically synthesized in large amounts. We used the fluorescein conjugated Lifeact (F-Lifeact) to label cells independently of genetic approaches. First, we tested if F-Lifeact could stain fixed cells and tissue sections. To compare F-Lifeact with the commonly used F-actin probe phalloidin directly, we performed double staining with Cy3-conjugated phalloidin on paraformaldehyde (PFA) fixed MDCK cells. Using TIRF microscopy to visualize the cell surface selectively, we observed nearly complete overlap of the two markers on the patch-like structures of the cortical actin network and in stress fibres (FIG. 4 a). We further double stained PFA fixed tissue sections of heart and skeletal muscle from mice and found a similar overlap of the actin probes in a banded pattern (FIG. 4 b). These findings demonstrate that the F-Lifeact peptide can be used as a non-toxic equivalent to phalloidin.

We next used the F-Lifeact peptide for loading into live cells and subsequent dynamic imaging. We performed so-called "scrape loading" (ref) of fibroblasts, MDCK cells and human neutrophils. This procedure allows diffusion of the peptide into the cytoplasm through transient membrane pores caused by mechanical removal of adherent cells from the culture dish. To avoid artefacts due to membrane damage after scrape loading or excessive loading of cells with peptide we concentrated on weakly labelled cells and used TIRF microscopy to observe actin structures. Fibroblasts scrape loaded with F-Lifeact revealed the typical distribution of F-actin in stress fibres and lamellipodia (FIG. 4c). The fluorescence signal was maintained over 4-6 hours before degradation of peptide and/or fading of the fluorochrome. In scrape loaded human neutrophils we were able to show for the first time the rapid dynamics of actin in these cells that exhibited extensive undirected lamellar protrusions after attaching to the culture dish (FIG. 4d).

2.5 Biological Validation

Neutrophils represent key players of the innate immune response and contribute to the tissue repair system of the body (25). The rapid polymerization of actin filaments is fundamental to neutrophil effector functions, e.g., extravasation, chemotaxis and phagocytosis. Since neutrophils are terminally differentiated and therefore non-transfectable, the current knowledge about neutrophil actin reorganization in response to chemotactic stimuli is mainly based on studies using HL-60 cells, a neutrophil-like myeloid tumour cell line (26). Furthermore, the integrin-dependent cytoskeletal reorganization in response to immune complex (IC) deposits has only been studied on fixed cells using fluorescent phalloidin reagents (27). Using F-Lifeact we were able, for the first time, to show actin dynamics in isolated human neutrophils and during their spreading on ICs. To validate the new probe we analyzed F-Lifeact loaded human neutrophils spreading on immune complexes. Using TIRF microscopy we observed two F actin populations in the spreading cells. Peripheral areas spread out rapidly with a speed of 14.1±2.8 µm/min (n=10), while there were no signs of retrograde actin transport (FIG. 5a, c). In central areas stationary patches formed that rapidly extended into the periphery after cells stopped spreading (FIG. 5b, d, extension stopped at the 10 s time point).

We next analyzed Lifeact-G transfected dendritic cells during phases of lamellipodial protrusion. Kymographic analysis in an area of lamellipodial protrusion and subsequent retraction (FIG. 5e, f) showed that dendritic cells do not show a clear distinction between a leading lamellipodium and a lamella, in contrast to data recently published for fibroblasts. We could not detect signs of periodic extension-retraction cycles as was demonstrated in spreading fibroblasts. Force generation for lamellipodial extension clearly did not depend on retrograde actin flow, as during extension the actin network did not move relative to the substrate. Hence, lamellipodial extension occurred with velocities (4 µm/min) that were comparable with the speed of retrograde flow during retraction or stagnation of the cell edge. Extension in the absence of retrograde flow is in line with recent findings that leukocyte migration does not depend on receptor mediated force coupling of the leading edge to the substrate (28).

3. Discussion

We have developed a novel actin probe, Lifeact, which is superior to currently available probes in several ways. Lifeact only consists of 17aa and represents the smallest available actin probe to date. It is easy to synthesize, both as oligonucleotide for generation of fusion proteins or as chemically labelled peptide. This makes Lifeact derived probes cost effective and widely accessible. The simple synthesis of a linear 17aa peptide, which can then easily be derivatized opens up new possibilities for the generation of actin-directed markers or drugs. As a consequence of its small size Lifeact can be easily delivered into cells. Transgenic fusion of the Lifeact coding sequence to fluorescent proteins yields higher expression levels than large cDNAs. We successfully introduced Lifeact-G into all major mammalian cell lineages. We also found that F-Lifeact peptide can be used to stain actin in fixed or live mammalian cells as well as in *Xenopus laevis* oocytes (our unpublished observation). Lifeact, therefore, is an alternative to the widely used cyclic peptide actin-probe phalloidin, which is usually purified from its biological source, the mushroom *Amanita phalloides*, because its synthesis is difficult.

The signal we obtained from Lifeact-G was specific for F-actin structures and exhibited very low cytosolic background. In contrast actin GFP was usually expressed at lower levels and signals suffered from high background staining of G-actin, especially when using widefield optics. Likewise, using F-Lifeact peptide we did not observe any nonspecific labelling in histology as well as in both PFA fixed and living cells.

The most important advantage of Lifeact as an actin probe in living cells is the lack of detectable interference with cellular processes. We could not measure significant effects of Lifeact expression on cytoskeletal dynamics, cell polarization or cell migration when we expressed Lifeact-G in living cells. Even sensitive processes such as neuronal polarization or leukocyte chemotaxis were undisturbed in the presence of high levels of Lifeact while lower fluorescent levels of actin GFP significantly influenced both processes. The observation that Lifeact does not alter actin dynamics at the cellular level is consistent with its low binding affinity to actin in vitro and the lack of effects on actin polymerization and depolymerization. This feature is unique among available actin probes and makes it non toxic which is an advantage during production and handling. In addition Lifeact has no homologous sequences in higher eukaryotes, which makes competition with endogenous proteins less likely.

REFERENCES

1. Bamburg, J. R. & Wiggan, O. P. ADF/cofilin and actin dynamics in disease. *Trends Cell Biol* 12, 598-605 (2002).
2. Laing, N. G. Congenital myopathies. *Curr Opin Neurol* 20, 583-589 (2007).
3. Suresh, S. Biomechanics and biophysics of cancer cells. *Acta Biomater* 3, 413-438 (2007).
4. Weinzierl, G. et al. Regulation of cell separation in the dimorphic fungus *Ustilago maydis*. *Mol Microbiol* 45, 219-231 (2002).
5. Waterman-Storer, C. M., Desai, A., Bulinski, J. C. & Salmon, E. D. Fluorescent speckle microscopy, a method to visualize the dynamics of protein assemblies in living cells. *Curr Biol* 8, 1227-1230 (1998).
6. Schmit, A. C. & Lambert, A. M. Microinjected fluorescent phalloidin in vivo reveals the F-actin dynamics and assembly in higher plant mitotic cells. *Plant Cell* 2, 129-138 (1990).
7. Yamada, S., Pokutta, S., Drees, F., Weis, W. I. & Nelson, W. J. Deconstructing the cadherin-catenin-actin complex. *Cell* 123, 889-901 (2005).
8. Edwards, K. A., Demsky, M., Montague, R. A., Weymouth, N. & Kiehart, D. P. GFP-moesin illuminates actin cytoskeleton dynamics in living tissue and demonstrates cell shape changes during morphogenesis in *Drosophila*. *Dev Biol* 191, 103-117 (1997).
9. Bretschneider, T. et al. Dynamic actin patterns and Arp2/3 assembly at the substrate-attached surface of motile cells. *Curr Biol* 14, 1-10 (2004).

10. Lenart, P. et al. A contractile nuclear actin network drives chromosome congression in oocytes. *Nature* 436, 812-818 (2005).
11. Pang, K. M., Lee, E. & Knecht, D. A. Use of a fusion protein between GFP and an actin-binding domain to visualize transient filamentous-actin structures. *Curr Biol* 8, 405-408 (1998).
12. Burkel, B. M., von Dassow, G. & Bement, W. M. Versatile fluorescent probes for actin filaments based on the actin-binding domain of utrophin. *Cell Motil Cytoskeleton* 64, 822-832 (2007).
13. Kost, B., Spielhofer, P. & Chua, N. H. A GFP-mouse talin fusion protein labels plant actin filaments in vivo and visualizes the actin cytoskeleton in growing pollen tubes. *Plant J* 16, 393-401 (1998).
14. Sheahan, M. B., Staiger, C. J., Rose, R. J. & McCurdy, D. W. A green fluorescent protein fusion to actin-binding domain 2 of *Arabidopsis* fimbrin highlights new features of a dynamic actin cytoskeleton in live, plant cells. *Plant Physiol* 136, 3968-3978 (2004).
15. Holweg, C. L. Living markers for actin block myosin-dependent motility of plant organelles and auxin. *Cell Motil Cytoskeleton* 64, 69-81 (2007).
16. Ketelaar, T., Anthony, R. G. Hussey, P. J. Green fluorescent protein-mTalin causes defects in actin organization and cell expansion in *Arabidopsis* and inhibits actin depolymerizing factor's actin depolymerizing activity in vitro. *Plant Physiol* 136, 3990-3998 (2004).
17. Asakura, T. et al. Isolation and characterization of a novel actin filament-binding protein from *Saccharomyces cerevisiae. Oncogene* 16, 121-130 (1998).
18. Yang, H. C. & Pon, L. A. Actin cable dynamics in budding yeast. *Proc Natl Acad Sci USA* 99, 751-756 (2002).
19. Cooper, J. A., Walker, S. B. & Pollard, T. D. Pyrene actin: documentation of the validity of a sensitive assay for actin polymerization. *J Muscle Res Cell Motil* 4, 253-262 (1983).
20. Dyson, H. J., Rance, M., Houghten, R. A., Wright, P. E. & Lerner, R. A. Folding of immunogenic peptide fragments of proteins in water solution. II. The nascent helix. *J Mol Biol* 201, 201-217 (1988).
21. Czisch, M., Schleicher, M., Horger, S., Voelter, W. & Holak, T. A. Conformation of thymosin beta 4 in Water determined by NMR spectroscopy. *Eur J Biochem* 218, 335-344 (1993).
22. Hertzog, M. et al. The beta-thymosin/WH2 domain; structural basis for the switch from inhibition to promotion of actin assembly. *Cell* 117, 611-623 (2004).
23. Irobi, E. et al. Structural basis of actin sequestration by thymosin-beta4: implications for WH2 proteins. *EMBO J* 23, 3599-3608 (2004).
24. Fischer, M., Haase, I., Wiesner, S. & Muller-Taubenberger, A. Visualizing cytoskeleton dynamics in mammalian cells using a humanized variant of monomeric red fluorescent protein. *FEBS Lett* 580, 2495-2502 (2006).
25. Nathan, C. Neutrophils and immunity: challenges and opportunities. *Nat Rev Immunol* 6, 173-182 (2006).
26. Weiner, O. D. et al. Spatial control of actin polymerization during neutrophil chemotaxis. *Nat Cell Biol* 1, 75-81 (1999).
27. Tang, T. et al. A role for Mac-1 (CDIIb/CD18) in immune complex-stimulated neutrophil function in vivo: Mac-1 deficiency abrogates sustained Fcgamma receptor-dependent neutrophil adhesion and complement-dependent proteinuria in acute glomerulonephritis. *J Exp Med* 186, 1853-1863 (1997).
28. Smith, L. A., Aranda-Espinoza, H., Haun, J. B., Dembo, M. & Hammer, D. A. Neutrophil traction stresses are concentrated in the uropod during migration. *Biophys J* 92, L58-60 (2007).
29. Janke, C. et al. A versatile toolbox for PCR-based tagging of yeast genes: new fluorescent proteins, more markers and promoter substitution cassettes. *Yeast* 21, 947-962 (2004).
30. Wüthrich, K. NMR of Proteins and Nucleic Acids (John Willey, New York 1986).
31. De Hoop, M. J., Meyn, L. & Dotti, C. G. in Cell Biology: A Laboratory Handbook. (ed. J. E. Cells) (Academic Press, San Diego, Calif.; 1997).
32. Bradke, F. & Dotti, C. G. in Microinjection and Transgenesis: Strategies and Protocols. (ed. A.C.-A.a.A. Garcia-Carrancá) 81-94 (Springer-Verlag, Heidelberg; 1998).

The invention claimed is:

1. A nucleic acid molecule encoding a peptide consisting of the amino acid sequence:

(M)$_n$ X$_1$ V A D L I X$_2$ K F E X$_3$ X$_4$ X$_5$ X$_6$ X$_7$ X$_8$ X$_{9-41}$;

wherein:
n is 0 or 1,
X$_1$ is selected from the group consisting of S and G,
X$_2$ is selected from the group consisting of K, Q and R,
X$_3$ is selected from the group consisting of S, K, Q, D and T,
X$_4$ is selected from the group consisting of I, F and Y,
X$_5$ is selected from the group consisting of S, A and T,
X$_6$ is selected from the group consisting of K, N, H and Q,
X$_7$ is selected from the group consisting of E, K, V, S and D,
X$_8$ is selected from the group consisting of E, K, D, S, G and P, and
X$_{9-41}$ are, in each occurrence, either absent or selected from the group consisting of A, R, N, D, C, Q, E, G, H, I, L, K, M, F, P, S, T, W, Y and V.

2. The nucleic acid molecule of claim 1, wherein amino acid residues 2-10 of the encoded peptide form an α-helical structure.

3. The nucleic acid molecule of claim 1, wherein the dissociation constant of the encoded peptide K$_d$ is ≤50 μM.

4. The nucleic acid molecule of claim 1, wherein the encoded peptide has the amino acid sequence:

(M)$_n$ G V A D L I K K F E SISKEE[(M)$_n$-SEQ ID NO: 3];

wherein n is 0 or 1.

5. The nucleic acid molecule of claim 1, wherein the encoded peptide has a length of up to 20 amino acid residues.

6. The nucleic acid molecule of claim 1, wherein the nucleic acid is operatively linked to an expression control sequence.

7. The nucleic acid molecule of claim 1, wherein the encoded peptide is multimerised.

8. A nucleic acid molecule encoding a peptide coupled to at least one heterologous peptide or heterologous polypeptide, wherein the peptide consists of the amino acid sequence:

(M)$_n$ X$_1$ V A D L I X$_2$ K F E X$_3$ X$_4$ X$_5$ X$_6$ X$_7$ X$_8$ X$_{9-41}$;

wherein:
n is 0 or 1,
X$_1$ is selected from the group consisting of S and G,
X$_2$ is selected from the group consisting of K, Q and R,
X$_3$ is selected from the group consisting of S, K, Q, D and T,
X$_4$ is selected from the group consisting of I, F and Y,
X$_5$ is selected from the group consisting of S, A and T,
X$_6$ is selected from the group consisting of K, N, H and Q,
X$_7$ is selected from the group consisting of E, K, V, S and D,
X$_8$ is selected from the group consisting of E, K, D, S, G and P, and
X$_{9-41}$ are, in each occurrence, either absent or selected from the group consisting of A, R, N, D, C, Q, E, G, H, I, L, K, M, F, P, S, T, W, Y and V.

9. The nucleic acid molecule of claim 8, wherein the at least one heterologous polypeptide is a fluorescent heterologous polypeptide.

10. The nucleic acid molecule of claim 8, wherein the at least one heterologous peptide or heterologous polypeptide is coupled to the N-terminus of the peptide, C-terminus of the peptide, or both the N-terminus and C-terminus of the peptide.

11. A recombinant cell comprising the nucleic acid molecule of claim 1.

12. A recombinant cell comprising the nucleic acid molecule of claim 2.

13. A recombinant cell comprising the nucleic acid molecule of claim 3.

14. A recombinant cell comprising the nucleic acid molecule of claim 4.

15. A recombinant cell comprising the nucleic acid molecule of claim 5.

16. A recombinant cell comprising the nucleic acid molecule of claim 6.

17. A recombinant cell comprising the nucleic acid molecule of claim 7.

18. A recombinant cell comprising the nucleic acid molecule of claim 8.

19. A recombinant cell comprising the nucleic acid molecule of claim 9.

20. A recombinant cell comprising the nucleic acid molecule of claim 10.

21. A non-human transgenic organism comprising the nucleic acid molecule of claim 1.

22. A non-human transgenic organism comprising the nucleic acid molecule of claim 8.

* * * * *